United States Patent [19]

Bánfi et al.

[11] Patent Number: 4,503,047
[45] Date of Patent: Mar. 5, 1985

[54] COMPOSITIONS FOR STIMULATING KERATIN FORMATION IN HAIR BULBS EMPLOYING HORSERADISH AND MUSTARD SEED EXTRACTS

[75] Inventors: András Bánfi, Békéscsaba; János Leibinger, Budapest; László Molnár, Budapest; Gizella Nádori née Kozel, Budapest; Sándor Tar, Balmazujváros, all of Hungary

[73] Assignee: Licencia Találmányokat Értékesitö Vállalat, Budapest, Hungary

[21] Appl. No.: 470,997

[22] Filed: Mar. 1, 1983

Related U.S. Application Data

[63] Continuation of Ser. No. 256,823, Apr. 23, 1981, abandoned.

[30] Foreign Application Priority Data

Apr. 28, 1980 [HU] Hungary .................... 1047/80

[51] Int. Cl.³ ............................................. A61K 35/78
[52] U.S. Cl. .................................................. 424/195.1
[58] Field of Search ........................................ 424/195

[56] References Cited

U.S. PATENT DOCUMENTS 4,169,073  9/1979  Mussinan et al. .................... 424/49

Primary Examiner—Allen J. Robinson
Assistant Examiner—John W. Rollins
Attorney, Agent, or Firm—Burton E. Levin

[57] ABSTRACT

The invention relates to a hair growth stimulating composition with improved properties, which contains horse radish extract in an aqueous-alcoholic solution optionally together with additives commonly applied in the preparation of hair growth stimulating agents. The composition according to the invention contains, beside the above ingredients 8 to 2000 mg/l, preferably 35 to 100 mg/l, of allyl isothiocyanate and 600 to 6000 mg/l, preferably 1100 to 2200 mg/l, of one or more sulfur-containing amino acid(s), and optionally up to 160 mg/l, preferably 1.5 to 6 mg/l, of copper(II) ions and up to 28 mg/l, preferably 1 to 5 mg/l, of rhodanide ions.

The invention also relates to a process for the preparation of the above composition.

The composition according to the invention is devoid of the disadvantage of Bánfi hair-lotion, since it does not make the hair tacky, does not render the scale sensitive to ultraviolet radiation, and has no unpleasant smell. Moreover, the hair growth stimulating effects of the new composition are more favorable than those of Bánfi hair-lotion.

15 Claims, No Drawings

COMPOSITIONS FOR STIMULATING KERATIN FORMATION IN HAIR BULBS EMPLOYING HORSERADISH AND MUSTARD SEED EXTRACTS

This is a continuation of copending application Ser. No. 256,823, filed Apr. 23, 1981, now abandoned.

The invention relates to a hair growth stimulating composition with improved properties, as well as to a process for the preparation thereof.

The Hungarian patent specification No. 169,439 describes a hair growth stimulating composition which contains horse radish extract as active component in an aqueous-alcoholic solution, optionally together with additives conventionally applied in the preparation of hair growth stimulating agents, preferably orange-peel extract, lemon-peel extract, egg-yolk and odouring substances. This composition is marketed under the trade mark "Banfi hair-lotion".

The composition disclosed in the Hungarian patent specification No. 169,439 is termed in the following as "Banfi hair-lotion" or "basic composition".

Banfi hair-lotion proved to be effective in the most diverse cases of hair fall and getting bald. The active agents of horseradish extract, including sulfur-containing amino acids and potassium rhodanide (KSCN) enter the organism by absorption through the treated area and have no harmful effect. It is a further advantage that in the preparation of the hair-lotion cheap and easily available substances are applied. Banfi hair-lotion has, however, the disadvantages that is has a very strong penetrating smell, and it makes the hair tacky which cannot be eliminated easily. This tackiness impedes the breathing of the scalp as well. The basic composition renders the scalp sensitive to ultra-violet radiation, giving rise to skin inflammations, therefore it is recommended to use the lotion primarily in seasons free of sunshine, particularly in winter. The storage stability of Banfi hair-lotion is insufficient; according to our experiences it cannot be stored for more than 8 months. Finally, Banfi hair-lotion is less effective or even ineffective in certain complaints connected with hair growth, primarily in pathological hair fall.

The invention aims at the elimination of the disadvantages of the composition disclosed in the Hungarian patent specification No. 169,439. The invention provides a composition which has no unpleasant smell, does not make the hair tacky, can be applied also in seasons with strong sunshine, even in summer, has a storability of more than one year, and possesses more favourable hair growth stimulating properties than the basic composition.

The invention is based on the following recognitions:

(a) The keratin-forming ability of the hair bulbs can be stimulated by adding allyl isothiocyanate to the basic composition.

(b) The keratin-forming ability of the hair bulbs can be further favourably influenced by augmenting the active agents in the mixture of allyl isothiocyanate and horseradish extract by adding rhodanide ion(s), copper (II) ion(s), sulfur-containing amino acid(s) or mixtures thereof.

(c) The unpleasant smell of horse radish extract can be covered by adding juniper berry extract to the basic composition, and simultaneously keratin formation can be accelerated.

(d) We have found that the light sensitizing effect of the basic composition is due to the presence of coumarin. This harmful effect can be avoided by removing sedimented coumarin from the composition and/or by adding a light protective agent, such as "Prosolal", a trademark for 5-(3,3-dimethyl-2-norbornylidene)-3-penten-2-one.

(e) We also have found that the tackiness of the hair is caused by plant proteins dissolved or suspended in the basic composition. Thus, if these proteins are removed (e.g., by sedimentation and filtration), this unpleasant phenomenon can be avoided.

(f) Finally, we have found that the limited storability of Banfi hair-lotion can be attributed to the decomposition of the plant proteins present. Thus, by removing these proteins, not only the tackiness can be avoided but the storability of the composition can also be improved.

Based on the above, the invention relates to a hair growth stimulating composition with improved properties, which contains horse radish extract in an aqueous-alcoholic solution, optionally together with additives commonly applied in the preparation of hair growth stimulating agents. The composition according to the invention contains, beside the above ingredients, 8 to 2000 mg/l, preferably 35 to 100 mg/l, of allyl isothiocyanate and 600 to 6000 mg/l, preferably 1100 to 2200 mg/l, of one or more sulfur-containing amino acid(s), and optionally up to 160 mg/l, preferably 1.5 to 6 mg/l, of copper(II) ions and up to 28 mg/l, preferably 1 to 5 mg/l, of rhodanide ions.

The term "sulfur-containing amino acid(s)" refers to amino acids which form a precipitate with silver nitrate.

Furthermore, the invention relates to a process for the preparation of a hair growth stimulating composition as defined above. According to the invention a horse radish extract prepared from 600 to 800 g of horse radish with 55 to 70% ethanol, which optionally contains additives commonly applied in the preparation of hair growing and hair growth stimulating agents, is admixed with 8 to 2000 mg/l, preferably 35 to 100 mg/l, of allyl isothiocyanate and an extract prepared from 25 to 60 g, preferably 30 to 45 g, of juniper berry and 25 to 60 g, preferably 30 to 45 g, of dried majoram leaves with 200 to 300 ml of 55 to 70% ethanol, preferably 60% ethanol, the resulting solution is optionally cooled to a temperature below 10° C., preferably to 4°-6° C., and the separated precipitate containing coumarin, starch and plant protein is removed from the solution.

Allyl isothiocyanate or a part thereof is added to the basic composition preferably in the form of mustard-seed extract.

The desired content of copper (II) ion or a part thereof can be obtained by adding a copper (II) salt, such as copper (II) sulfate monohydrate, or preferably, by adding an alcohol extract of marjoram. The sulfur-containing amino acid and rhodanide ion content of the mixture of allyl isothiocyanate and basic composition can be augmented by adding any sulfur-containing amino acid, such as L-cysteine or DL-methionine, and a soluble rhodanide salt, such as potassium rhodanide.

According to a preferred method of the invention one proceeds so that an extract prepared from 560 kg of horse radish with 800 liters of 60% ethanol (basic composition) is admixed with an extract prepared from 40 kg of mustard-seed, 20 kg of juniper berry and 20 kg of majoram with 200 liters of 60% ethanol. The resulting solution is cooled to 5° C., and the separated precipitate is removed by filtration.

By this method a clear, light reddish-brown coloured solution is obtained with a pleasant odour resembling juniper tree, free of the unpleasant smell of horse radish. This composition does not cause tackiness when applied onto the scalp or hair, and can be stored for at least 12 months without any physical change or loss in activity. This composition does not render the scalp sensitive to ultraviolet radiation. Furthermore, in contrast to the basic composition, the new composition is effective even in pathological hair fall.

The favourable biological properties of the new composition in comparison with the basic composition are proved by the results of physiological tests.

The physiological tests were performed at the dermatological department of the Semmelweis University of Medical Sciences, Budapest. 10 patients each were treated with the new composition and with the basic composition under identical conditions. The patients required treatment because of diffuse and/or local hair loss (alopecia areata) or seborrhoeal hair loss (alopecia seborrhoeica).

The nature, beginning and approximate degree of hair fall, the medicines taken by the patients and eventual other disorders were recorded first for all of the patients. Prior to the start of the treatment a pre-determined number of capilli were removed from the appropriate area together with the hair bulb.

The hair samples to be examined were taken from the following areas:
  patients with diffuse hair fall: top of the head
  patients with local hair fall: surroundings of the bald spot
  patients with simultaneous diffuse and local hair fall: top of the head
  patients with seborrhoeal hair fall: thinned area of the hair Patients with diffuse and seborrhoeal hair fall were treated once a week so that the scalp was rubbed thoroughly with the composition one hour prior to hair washing, and this rubbing was repeated twice more in every 20 minutes. Patients with local hair fall were treated twice a day, whereas patients with simultaneous local and diffuse hair fall were treated once a week. The patients were examined in every second week. At that time the changes observed by the patient were recorded, furthermore the state of the patient was checked clinically, and hair samples were taken for trichological examination. The number of examinations varied between 2 and 7, thus the duration of the treatment varied between 2 and 12 weeks.

The clinical and trichological examinations were performed with the compositions prepared according to Example 1 of the present specification and Example 1 of the Hungarian patent specification No. 169,439, respectively. The results are listed in Tables 1 and 2.

TABLE 1

| | Clinical test results | |
| Qualification | Basic composition | Composition of the invention |
| --- | --- | --- |
| Unchanged | 28% | — |
| Partial improvement | 54% | 56% |
| Complete improvement (cured) | 18% | 44% |

The term "unchanged" refers to patients on which no change appeared upon the treatment. The term "partial improvement" refers to patients on which the degree of hair fall decreased upon the treatment, but did not stop. The term "complete improvement (cured)" refers to patients on which hair fall stopped completely or decreased to the normal level, or even hair growth started.

In the trichological tests the structure and state of the capilli as well as the state of the hair bulbs were examined. Furthermore, the ratio of growing active (anageneous) capilli and those in the repose state (telogeneous capilli) was determined, and the change in this ratio was followed up during the examination period. The capilli to be examined were placed, without pre-treatment, onto a microscopic slide and covered with Canada balm.

TABLE 2

| | Results of trichological examinations | |
| Qualification | Basic composition | Composition of the invention |
| --- | --- | --- |
| Unchanged | 64% | 11% |
| Partial improvement | 27% | 67% |
| Complete improvement (cured) | 9% | 22% |

According to literature data the ratio of anagenous and telogenous capilli varies between 8:2 and 9:1 for normal human hair. Thus those patients were classified as "cured" for whom this ratio raised to at least 7:3 from the initial low value. Those patients for whom the ratio varied between 5:5 and 6:4 were qualified as "partially improved", whereas patients with a lower ratio were qualified as "unchanged".

The data of Tables 1 and 2 prove unambiguously that the composition according to the invention provides much more favourable results in both the clinical and the trichological examinations than the basic composition. Furthermore, none of the patients treated with the composition according to the invention complained of a burning, itching feel on the scalp treated, whereas numerous patients treated with the basic composition had such complaints.

The major advantages of the composition according to the invention are as follows:

(a) It exerts more favourable hair growth stimulating effects than the basic composition.

(b) It has no unpleasant smell.

(c) It does not make the hair tacky.

(d) It can be stored for more than one year.

(e) It does not render the scalp sensitive to ultraviolet radiation, thus it can also be applied in seasons with sunshine, even in summer.

The invention is elucidated in detail by the aid of the following non-limiting Examples.

EXAMPLE 1

670 kg of edible horse radish, cut ot cubes 1–3 cm in edge length, are macerated with 1150 liters of 60% ethanol for 5 days. The container is moved at least once a day. After 5 days the macerate is separated from the solids by filtration.

A mixture of 200 kg of white mustard-seed, 100 kg of juniper berry (comminuted in a hammer mill), 100 kg of majoram and 1150 liters of 60% ethanol is allowed to stand at room temperature for 5 days. Thereafter the solids are removed by filtration from the extract. 200 liters of the resulting extract are admixed with 800 liters of the horse radish extract, and 5 kg of "Prosolal" (a light protective agent) are dissolved in the composition. 40 kg of granular aluminium oxide are added to the solution, the mixture is stirred thoroughly, and aluminium oxide is allowed to settle. The mixture is filtered through a fine flat filter.

The resulting light brownish-red solution contains 35 mg/l of allyl isothiocyanate, 1.6 mg/l of copper(II) ions, 1 mg/l of rhodanide ions and 1850 mg/l of sulfur-containing amino acid(s).

EXAMPLE 2

A mixture of 552 kg of cut edible horse radish, 50 kg of mustard-seed, 30 kg of crushed juniper berry and 1150 liters of 60% ethanol is allowed to stand at room temperature for 5 days. Thereafter the macerate is filtered, cooled to 5° C., and filtered immediately through a sieve with a gap size of 0.5 mm. 44 kg of granular aluminium oxide are admixed with the filtrate, and the mixture is filtered through a flat filter as described in Example 1. The resulting slightly brownish-red, transparent solution contains 15 mg/l of allyl isothiocyanate, 1.2 mg/l of copper(II) ions, 1500 mg/l of sulfur-containing amino acid(s) and 0.05 mg/l of rhodanide ions.

EXAMPLE 3

One proceeds as described in Example 1 with the difference that maceration is started with 729 liters of 96% ethanol for both the horse radish and the mixture of white mustard-seed, juniper berry and majoram, and the amount of tap water (431 liters) required to set the alcohol concentration to 60% is added only after 3 hours of standing.

The resulting solution can be stored for a much longer period than that prepared according to Example 1, since the major part of the plant proteins affecting the storability are precipitated already during the first ethanol treatment.

The composition of the resulting solution is essentially the same as that of the solution obtained according to Example 1.

EXAMPLE 4

A mixture of 690 kg of comminuted edible horse radish and 9 kg of white mustard-seed is macerated with 1150 liters of 60% ethanol without heating. After 5 days of maceration the solids are removed by filtration, and the resulting extract, about 1000 liters in volume, is admixed with 10 kg of juniper berry oil and 5 kg of a light protective agent sold under the trade name "Prosolal".

3000 g of L-cysteine and 2000 g of DL-methionine are dissolved in 10 liters of 60% ethanol, and the solution is admixed with the above macerate.

The resulting composition contains 8 mg/l of allyl isothiocyanate and 6000 mg/l of sulfur-containing amino acids.

EXAMPLE 5

One proceeds as described in Example 1 with the difference that 414 g of copper(II) sulfate monohydrate are dissolved in the product.

The resulting composition contains 35 mg/l of allyl isothiocyanate, 150 mg/l of copper(II) ions, 1 mg/l of rhodanide ions and 1850 mg/l of sulfur-containing amino acid(s).

EXAMPLE 6

One proceeds as described in Example 1 with the difference that 40 g of potassium rhodanide and 1925 g of allyl isothiocyanate are dissolved in the product under steady stirring.

The resulting composition contains 1960 mg/l of allyl isothiocyanate, 1.6 mg/l of copper(II) ions, 25 mg/l of rhodanide ions and 1850 mg/l of sulfur-containing amino acid(s).

EXAMPLE 7

A macerate is prepared from 690 kg of comminuted edible horse radish and 9 kg of white mustard-seed with 1150 liters of 60% ethanol at room temperature. After 5 days of maceration the solids are filtered off, and the resulting extract, about 1000 liters in volume, is admixed with 10 kg of juniper berry oil and 5 kg of a light protective agent sold under the trade name "Prosolal".

The product contains 8 mg/l of allyl isothiocyanate and 700 mg/l of sulfur-containing amino acid(s).

What we claim is:

1. Composition for stimulating keratin formation in hair bulbs comprising aqueous alcohol and the portion of edible horseradish which is soluble in 55 to 70% aqueous ethanol, characterized by also containing 8 to 2000 mg/l of allyl isothiocyanate and 600 to 6000 mg/l of at least one sulfur-containing amino acid selected from the group consisting of L-cysteine and DL-methionine.

2. A composition as claimed in claim 1, characterized by containing 35 to 100 mg/l of allyl isothiocyanate.

3. A composition as claimed in claim 1, characterized by containing 1100 to 2200 mg/l of at least one sulfur-containing amino acid selected from the group consisting of L-cysteine and DL-methionine.

4. A composition as claimed in claim 1, characterized by also containing up to 160 mg/l of copper (II) ions.

5. A composition as claimed in claim 4, characterized by containing 1.5 to 6 mg/l of copper (II) ions.

6. A composition as claimed in claim 1, characterized by also containing up to 28 mg/l of rhodanide ions.

7. A composition as claimed in claim 6, characterized by containing 1 to 5 mg/l of rhodanide ions.

8. Composition for stimulating keratin formation in hair bulbs comprising 55 to 70% aqueous ethanol and the portion of edible horseradish which is soluble in said aqueous ethanol, characterized by also containing 35 to 100 mg/l of allyl isothiocyanate and 1100 to 2200 mg/l of at least one sulfur-containing amino acid selected from the group consisting of L-cysteine and DL-methionine.

9. A process characterized in that a horseradish extract prepared by extracting 600 to 800 g of horseradish with 55 to 70% ethanol is admixed with 8 to 2000 mg/l of allyl isothiocyanate and a second extract prepared by extracting 25 to 60 g of juniper berry and 25 to 60 g of dried marjoram leaves with 200 to 300 ml of 55 to 70% ethanol, the resulting solution is cooled to a temperature below 10° C., and the separated precipitate is removed from the solution.

10. A process as claimed in claim 9, characterized in that 35 to 100 mg/l of allyl isothiocyanate is added.

11. A process as claimed in claim 9, characterized in that the total amount of allyl isothiocyanate or a part thereof is added in the form of mustard seed extract prepared by extracting mustard seed with aqueous alcohol.

12. A process as claimed in claim 9, characterized in that 30 to 45 g of juniper berry are used to form the second extract.

13. A process as claimed in claim 9, characterized in that 30 to 45 g of dried marjoram leaves are used to from the second extract.

14. A process as claimed in claim 9, characterized in that the second extract is prepared with 60% ethanol.

15. A process as claimed in claim 9, characterized in that the solution is cooled to 4° to 6° C.

* * * * *